United States Patent [19]
Koyama

[11] 4,030,665
[45] June 21, 1977

[54] APPARATUS FOR FOAMING LIQUID COSMETIC SUBSTANCES

[75] Inventor: Masaya Koyama, Osaka, Japan

[73] Assignee: Goldwell GmbH, Darmstadt-Eberstadt, Germany

[22] Filed: July 9, 1975

[21] Appl. No.: 594,468

[52] U.S. Cl. ................................ 239/373; 222/195; 222/333; 239/332; 239/602; 252/359 A; 252/359 E; 261/DIG. 26

[51] Int. Cl.² .................... A61M 11/02; B05B 9/04; B01F 5/18

[58] Field of Search .................... 252/359 A, 359 E; 239/332, 343, 370, 373, 375, 602; 222/195, 333; 261/DIG. 26

[56] References Cited

UNITED STATES PATENTS

| | | | |
|---|---|---|---|
| 3,120,347 | 2/1964 | Duke, Jr. | 239/332 |
| 3,122,325 | 2/1964 | Mahrt et al. | 239/343 |
| 3,332,457 | 7/1967 | Nisbet et al. | 239/602 X |
| 3,447,754 | 6/1969 | Nohl | 239/343 |
| 3,472,425 | 10/1969 | Booth et al. | 222/195 X |
| 3,472,455 | 10/1969 | Johnson et al. | 222/195 X |
| 3,572,660 | 3/1971 | Mahon et al. | 239/370 X |
| 3,680,789 | 8/1972 | Wagner | 239/332 |
| 3,931,914 | 1/1976 | Hosaka et al. | 222/333 |

*Primary Examiner*—Morris O. Wolk
*Assistant Examiner*—Michael S. Marcus
*Attorney, Agent, or Firm*—Allison C. Collard

[57] ABSTRACT

An apparatus for foaming liquid cosmetic substances, comprising a vessel for receiving a supply of a cosmetic substance for application and an electrically driven pump merging into the vessel and having an exit side connected to the air supply duct. A foam generator in the form of a porous, open-cell member is immersed in the substance and disposed at an end of the air supply duct and is adapted to introduce the air stream supplied thereto by the pump into the substance in the form of a plurality of small bubbles. A delivery nozzle is connected to the vessel from which the foam developed in the vessel emerges.

7 Claims, 2 Drawing Figures

APPARATUS FOR FOAMING LIQUID COSMETIC SUBSTANCES

Figure 1:
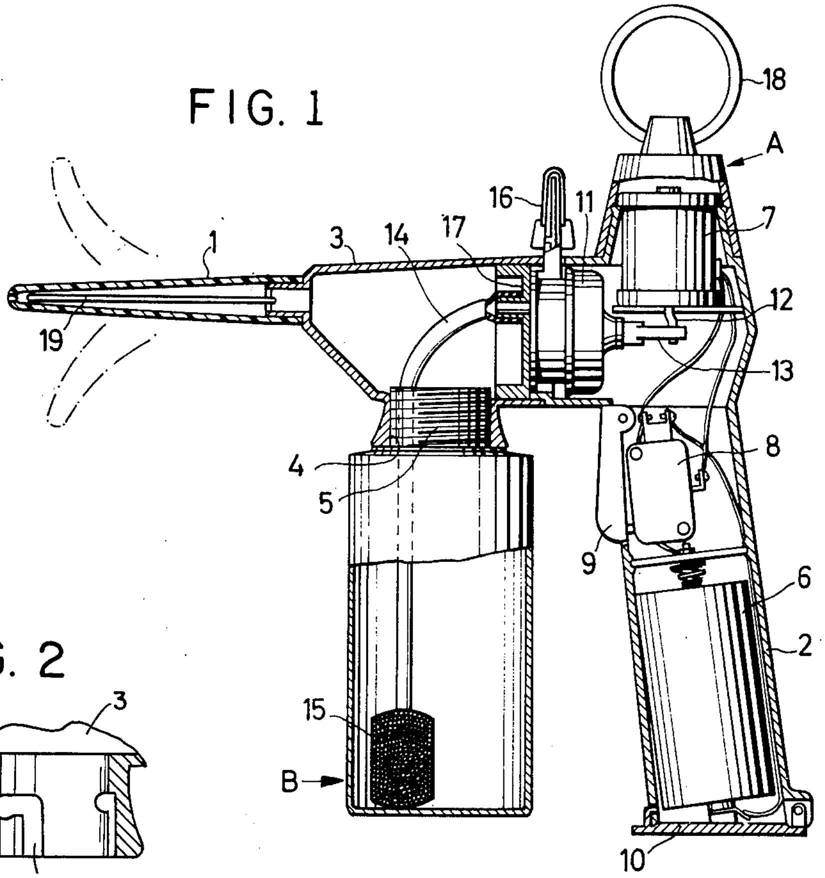

The invention relates to apparatus for foaming liquid cosmetic substances and for the intended application of the foam.

Specific liquid cosmetic substances, for example, permanent-wave liquid, fixing agents for permanent waves, toilet water and the like were hitherto applied exclusively in the liquid state with the disadvantage that the substance did not sufficiently adhere, dripped or ran off the treated parts of the hair or scalp, thus requiring re-wetting. This resulted not only in an increased consumption of the substance but also caused the dripping substance to affect parts of the skin for which the substance was not intended, thus leading to skin irritations due to the permanent-wave liquid, and more particularly in the case of sensitive persons. There is therefore a genuine requirement for a method for applying such substances in such a way that the applied substance adheres well at the intended place of application without losing its settability.

It is therefore the object of the invention to permit such improved local adhesion without the disadvantage of reduced action resulting from a deterioration in the wetting or moistening effect of such cosmetic substances.

Proceeding from the knowledge that foamed liquids do not tend to run off, more particularly if the foam bubbles are small, and nevertheless exhibit excellent wetting properties, it is an object and solution of this problem in accordance with the invention in that the substances, which were hitherto used only in their liquid form, are first converted into a foam of small bubbles and are then made to act in this form. The foam is in a device in which the cosmetic substance to be applied is stored, in a vessel connected to an air supply duct which extends from a delivery side of an electrically driven pump. A foam generator is immersed in the substance and takes the form of a porous, open-cell member being disposed at the end of the air supply duct and adapted to introduce the air stream supplied by the pump into the substance in the form of a plurality of small bubbles, and the vessel is associated with a delivery nozzle from which the foam, which is developed in the vessel emerges.

The apparatus according to the invention therefore blows ordinary ambient air into the substance, the air being so finely divided that the substance is foamed and accompanied by a large increase of its volume.

Surprisingly, it has been found that these foams are sufficiently stable to adhere for the intended duration of action. Substantially smaller quantities of substance are therefore sufficient to achieve identical or improved results when compared to the application of liquid.

It is already known to deliver liquid soap substances in the form of foam from special aerosol spray cans, i.e., substances which are liquid under elevated pressure and are converted into the gaseous state when the pressure is reduced. However, this merely simulates the known foaming of soap in a form which is simplified for the user. However, numerous cosmetic substances are chemically incompatible with the aerosols which are available and the aerosols themselves represent a substantial cost factor apart from the fact that the latest knowledge does not preclude the possibility of such aerosols being responsible for environmental pollution. The pressurized cans which can be used only once also represent a substantial cost factor. By contrast, the gas used for foaming in the apparatus according to the invention is ordinary air which is universally available without cost. Pressure-tight vessels are not required and this apparatus having a relatively simple construction can be constantly re-used, so that the purchase cost can be written off in the shortest possible time merely on the basis of the reduced consumption of substances and more particularly when used by hairdressers, cosmetic institutes and the like.

In one advantageous embodiment of the invention the air pump can be driven by an electric motor which obtains its energy from a battery which can be inserted in the apparatus. The use of the apparatus is therefore not obstructed by an electric lead for connection to the mains.

A particularly convenient operation of the apparatus is obtained if the apparatus is constructed in the manner of a pistol with a handle. In this case the battery advantageously can be disposed in the handle.

In a further embodiment of the invention the apparatus is actuated by a switch which can be operated by a push-button operating element which provides the electrical connection between the battery and the motor when the push-button operating element is depressed.

A diaphram pump is advantageously employed as the air pump because such diaphram pumps not only operate reliably and have long service life, but also are relatively moderately priced.

It is also advantageous to arrange the vessel removably on a section of the device in which a space is formed which communicates with the delivery nozzle. In this way it is possible for the manufacturers to supply the substance in a vessel which can be connected directly to the device so that recharging, cleaning of the substance container and the like is eliminated, feature which also offers hygenic advantages. Screw connections or bayonet connections can be considered as advantageous connections between the substance vessel and the apparatus.

In one particularly advantageous embodiment of the invention, the delivery nozzle is situated at the end of an elongated tubular member made of resilient material which communicates with the space which in turn communicates with the vessel, and the interior of the tubular member contains a plastically deformable wire, corresponding approximately to the length of the member, bending of the wire resulting in corresponding bending of the member of resilient material. The discharge direction of the nozzle can thus be altered in relation to the position of the apparatus without the need for the apparatus to be pivoted or tilted in a manner which is inconvenient for the user.

Other objects and features of the present invention will become apparent from the following detailed description when taken in connection with the accompanying drawing which discloses several embodiments of the invention. It is to be understood that the drawing is designed for the purpose of illustration only, and is not intended as a definition of the limits and scope of the invention disclosed.

One embodiment in the drawing of which FIG. 1 is a partially sectioned side view of an embodiment of the apparatus according to the invention is illustrated.

Figure 2:
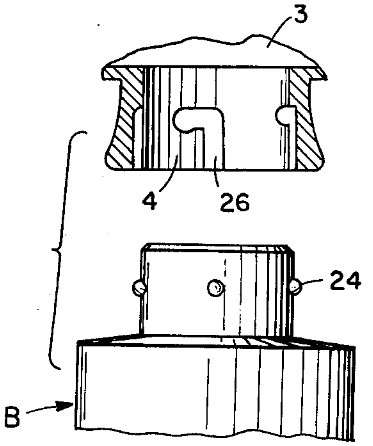

FIG. 2 is a detailed partial view of another embodiment of the invention illustrating an alternative vessel connection.

Referring now to the drawing, the illustrated embodiment of the apparatus according to the invention comprises a pistol-like housing A, having removably mounted thereon a vessel B for a cosmetic substance which is to be foamed. The foam generated in the apparatus is discharged from an elongated nozzle member 1 which communicates with a space formed in a housing part 3 which in turn has a connecting port 4 into which the neck of the vessel B, having screw-threads 5, can be screw-mounted. The handle 2, which is intended for gripping the apparatus, is mounted at an angle on the housing part 3. The hollow interior of the handle 2 is provided for the accommodation of an electric battery 6, which supplies the energy for an electric motor 7 disposed in the housing A. An electric switch 8, inserted into the electric conductors between the battery 6 and the motor 7, enables the device to be taken into operation through a push-button operating element 9.

A hinged lid 10 provided on the underside of the handle 2 enables spent batteries 6 to be exchanged.

The motor 7 drives an air pump which is constructed as a diaphram pump 11. The drive is provided through the cranked end 12 of the motor spindle and the pump tappet which is connected to the diaphram of the pump 11 and has an oscillating motion imparted to it by the motor spindle. The diaphram pump feeds into an air supply duct 14 which extends through the interior of the housing section 3 and the opening 4 into the interior of the vessel B, the bottom end of the supply duct supporting a foam generator 15 in the form of a porous, open-cell member through which the air stream, delivered via the air supply duct 14, is fed in the form of very fine bubbles into the cosmetic substance which is to be foamed. The foam produced thereby is discharged from the vessel B into the interior of the housing part 3 and emerges therefrom through the elongated nozzle member 1.

The pump 11 can be provided with an adjustable suction valve 16 for adjusting the amount of air which is delivered into the substance vessel B.

The transfer of foam into the apparatus part of the housing A containing the pump and the motor is prevented by a bulkhead 17 which separates the space formed in the interior of the housing part 3 with respect to the remainder of the housing.

A retaining ring 18 provided on the top of the apparatus enables the apparatus to be suspended near the intended working place in a manner convenient for gripping.

There is a special feature to be mentioned with respect to the elongated nozzle member 1 which can be constructed of flexible material, for example, a suitable plastic material. An elongated wire 19, which can be elastically bent, is disposed within the nozzle member 1 and enables the exit direction of the foam from the nozzle member 1 to be altered by suitable bending. Changed positions of the nozzle member 1 obtained by bending the wire 19 are shown in the drawing by dash-dot lines.

The embodiment shown in FIG. 2 is the same as the embodiment shown in FIG. 1, except that in place of the screw connection 5 of FIG. 1, a standard-type bayonet connection is shown. Vessel B is provided with prongs 24 adapted to engage recess 26 on connecting port 4 of the housing part 3. In all other respects, the FIG. 2 embodiment is the same as the FIG. 1 embodiment.

While only a single embodiment of the present invention has been shown and described, it will be obvious to those skilled in the art that many changes and modifications may be made thereunto without departing from the spirit and scope of the invention.

What is claimed is:

1. A portable hand-held electrical apparatus for foaming liquid cosmetic substances having a self-contained electrical supply, comprising:

a pistol-like housing including a housing part and a handle part, said housing part having an interior space, a bulkhead in said interior space separating said housing part into a pumping chamber and a flow communication chamber, said flow communication chamber having an inlet means and an outlet means;

a vessel connected to said inlet means for flow communication between said vessel and said flow communication chamber for supplying a supply of a cosmetic substance adapted to be foamed and removably connectable with said housing part;

an air supply duct having one end entering said vessel and another end connected to said bulkhead with the portion therebetween in said flow communication chamber;

air pump supply means including an electrically driven pump in said pumping chamber having an inlet communicating with the exterior of said housing part to obtain ambient air and an outlet operatively connected to said other end of said duct for passing an air stream into said duct through said flow communication chamber;

electrical supply containing means in said handle part including means connected to said electrically driven pump for energization thereof to drive said electrically driven pump;

said means to drive said pump comprising:

an electric motor for driving said pump, and a battery insertable into said electrical supply containing means for providing said self-contained electrical supply;

foam generator means in the form of a porous open-cell member immersed in the substance and being disposed at said one end of said air supply duct and receiving said air stream supplied thereto by said pump through said duct and introducing said air stream into the substance in the form of a plurality of small bubbles to produce foam; and a resilient delivery nozzle means connected to the outlet means of said flow communication chamber of said housing part and communicating with said vessel through said flow communication chamber for dispensing the foam developed in said vessel, said resilient delivery nozzle means being bendable in all directions for altering thereof in relation to the position of the hand-held apparatus.

2. The apparatus as recited in claim 1 wherein said means to drive said pump additionally comprises:

switch means in said handle part with a push-button operating element external of said handle part and connected therewith for establishing an electrical connection between said battery means and said motor means when said push-button operating element is actuated.

3. The apparatus as recited in claim 1 wherein said flow communication chamber comprises a separate space formed in said housing part which communicates with said delivery nozzle and said vessel, said vessel including a connector and said inlet means including a connection port, said vessel being connected by said connector to said housing and communicating with said separate space through said connection port.

4. The apparatus as recited in claim 3 wherein: said connector is a screw connection.

5. The apparatus as recited in claim 3 wherein: said connector is a bayonet connection.

6. The apparatus according to claim 3 wherein: said resilient nozzle comprises an elongated tubular member of flexible material communicating with said space, and an elastically bendable wire centrally disposed inside said tubular member, said bendable wire having a length corresponding approximately to that of said tubular member, whereby said wire when bent, causes a corresponding bending of said tubular member of flexible material.

7. The apparatus as recited in claim 1 wherein said air supply means includes;

a diaphram pump; and an adjustable suction valve means provided on said pump for changing the volume of air delivered by said pump to said duct.

* * * * *